United States Patent
Eversull et al.

(10) Patent No.: US 7,837,671 B2
(45) Date of Patent: Nov. 23, 2010

(54) SLITTABLE AND PEELABLE SHEATHS AND METHODS FOR MAKING AND USING THEM

(75) Inventors: Christian S. Eversull, Palo Alto, CA (US); Stephen A. Leeflang, Sunnyvale, CA (US); Nicholas J. Mourlas, Mountain View, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/617,163

(22) Filed: Nov. 12, 2009

(65) Prior Publication Data
US 2010/0057012 A1    Mar. 4, 2010

Related U.S. Application Data (63) Continuation of application No. 11/563,142, filed on Nov. 24, 2006, now Pat. No. 7,637,902.

(60) Provisional application No. 60/739,249, filed on Nov. 23, 2005.

(51) Int. Cl.
A61M 25/00    (2006.01)
(52) U.S. Cl. ..................... 604/524; 604/171
(58) Field of Classification Search .......... 600/433; 604/164.13, 171, 524; 623/1.23
See application file for complete search history.

(56) References Cited

U.S. PATENT DOCUMENTS

| | | |
|---|---|---|
| 4,392,853 A | 7/1983 | Muto |
| 4,401,433 A | 8/1983 | Luther |
| 4,406,656 A | 9/1983 | Hattler et al. |
| 4,451,256 A | 5/1984 | Weikl et al. |
| 4,569,347 A | 2/1986 | Frisbie |
| 4,601,713 A | 7/1986 | Fuqua |
| 4,631,059 A | 12/1986 | Wolvek et al. |
| 4,710,181 A | 12/1987 | Fuqua |
| 4,738,666 A | 4/1988 | Fuqua |
| 4,921,479 A | 5/1990 | Grayzel |
| 4,997,424 A | 3/1991 | Little |
| 5,015,239 A | 5/1991 | Browne |
| 5,125,904 A | 6/1992 | Lee |
| 5,158,545 A * | 10/1992 | Trudell et al. ............... 604/509 |
| 5,201,756 A | 4/1993 | Horzewski et al. |
| 5,234,425 A | 8/1993 | Fogarty et al. |
| 5,254,084 A | 10/1993 | Geary et al. |
| 5,256,150 A | 10/1993 | Quiachon et al. |
| 5,275,151 A | 1/1994 | Shockey et al. |

(Continued)

FOREIGN PATENT DOCUMENTS

EP    948970    10/1999

(Continued)

OTHER PUBLICATIONS

USPTO Office Action for co-pending U.S. Appl. No. 10/423,321 dated Oct. 24, 2006.

(Continued)

*Primary Examiner*—Nicholas D Lucchesi
*Assistant Examiner*—Gerald Landry, II (57) ABSTRACT

A sheath for delivering a lead or other device into a body lumen is adapted to be removed from around the delivered lead or device via a longitudinally extending feature. This feature of the sheath may be a ripcord, a seam or interlocking features the releasably engage one another.

3 Claims, 7 Drawing Sheets

U.S. PATENT DOCUMENTS

| | | | |
|---|---|---|---|
| 5,304,134 A | 4/1994 | Kraus et al. | |
| 5,312,355 A | 5/1994 | Lee | |
| 5,330,460 A | 7/1994 | Moss et al. | |
| 5,395,349 A | 3/1995 | Quiachon et al. | |
| 5,413,560 A | 5/1995 | Solar | |
| 5,431,676 A | 7/1995 | Dubrul et al. | |
| 5,472,418 A | 12/1995 | Palestrant | |
| 5,573,517 A | 11/1996 | Bonutti et al. | |
| 5,618,267 A | 4/1997 | Palestrant | |
| 5,674,240 A | 10/1997 | Bonutti et al. | |
| 5,827,227 A | 10/1998 | DeLago | |
| 5,911,702 A | 6/1999 | Romley et al. | |
| 5,944,691 A | 8/1999 | Querns et al. | |
| 5,961,499 A | 10/1999 | Bonutti et al. | |
| 5,997,508 A | 12/1999 | Lunn et al. | |
| 6,077,250 A * | 6/2000 | Snow et al. | 604/174 |
| 6,090,072 A | 7/2000 | Kratoska et al. | |
| 6,120,477 A | 9/2000 | Campbell et al. | |
| 6,159,198 A | 12/2000 | Gardeski et al. | |
| 6,183,443 B1 | 2/2001 | Kratoska et al. | |
| 6,197,016 B1 | 3/2001 | Fourkas et al. | |
| 6,258,061 B1 | 7/2001 | Drasler et al. | |
| 6,315,792 B1 * | 11/2001 | Armstrong et al. | 623/1.23 |
| 6,338,730 B1 | 1/2002 | Bonutti et al. | |
| 6,361,528 B1 | 3/2002 | Wilson et al. | |
| 6,497,681 B1 | 12/2002 | Brenner | |
| 6,544,247 B1 | 4/2003 | Gardeski et al. | |
| 6,652,492 B1 | 11/2003 | Bell et al. | |
| 6,712,791 B2 | 3/2004 | Lui et al. | |
| 6,814,715 B2 | 11/2004 | Bonutti et al. | |
| 6,939,327 B2 * | 9/2005 | Hall et al. | 604/164.05 |
| 7,166,099 B2 | 1/2007 | Devens, Jr. | |
| 2001/0007927 A1 | 7/2001 | Koblish et al. | |
| 2001/0039418 A1 | 11/2001 | Schaer | |
| 2001/0053919 A1 | 12/2001 | Keiturakis et al. | |
| 2002/0095117 A1 | 7/2002 | Wilson et al. | |
| 2002/0099431 A1 | 7/2002 | Armstrong et al. | |
| 2002/0165598 A1 | 11/2002 | Wahr et al. | |
| 2003/0050604 A1 | 3/2003 | Lui et al. | |
| 2003/0065353 A1 | 4/2003 | Horzewski et al. | |
| 2003/0158565 A1 | 8/2003 | Gardeski et al. | |
| 2003/0181935 A1 | 9/2003 | Gardeski et al. | |
| 2003/0212373 A1 * | 11/2003 | Hall et al. | 604/263 |
| 2003/0233115 A1 | 12/2003 | Eversull et al. | |
| 2004/0006344 A1 | 1/2004 | Nguyen et al. | |
| 2004/0073286 A1 | 4/2004 | Armstrong et al. | |
| 2004/0087968 A1 | 5/2004 | Core | |
| 2004/0176740 A1 | 9/2004 | Chouinard | |
| 2005/0059890 A1 * | 3/2005 | Deal et al. | 600/433 |
| 2005/0085842 A1 | 4/2005 | Eversull et al. | |
| 2005/0149104 A1 | 7/2005 | Leeflang et al. | |
| 2005/0149105 A1 | 7/2005 | Leeflang et al. | |
| 2005/0182387 A1 | 8/2005 | Webler | |
| 2005/0283136 A1 | 12/2005 | Skarda | |

FOREIGN PATENT DOCUMENTS

| | | |
|---|---|---|
| EP | 818214 | 4/2007 |
| WO | 84/01512 | 4/1984 |
| WO | 97/29680 | 8/1997 |
| WO | 98/29026 | 7/1998 |
| WO | 0103766 | 1/2001 |
| WO | 03090834 | 11/2003 |

OTHER PUBLICATIONS

USPTO Office Action for co-pending U.S. Appl. No. 10/958,034 dated Dec. 13, 2006.

* cited by examiner

FIG. 9B

SLITTABLE AND PEELABLE SHEATHS AND METHODS FOR MAKING AND USING THEM

The present application is a divisional of U.S. application Ser. No. 11/563,142, filed Nov. 24, 2006, which claims benefit of U.S. provisional application Ser. No. 60/739,249, filed Nov. 23, 2005, the entire disclosure of which is expressly incorporated by reference herein.

FIELD OF THE INVENTION

The present invention relates generally to apparatus and methods for delivering instruments and/or agents during a medical procedure, and, more particularly, to guide sheaths for accessing body lumens and/or delivering instruments into body lumens of a patient and to methods for making and using them.

BACKGROUND

Minimally invasive procedures have been implemented in a variety of medical settings, e.g., for vascular interventions, such as angioplasty, stenting, embolic protection, electrical heart stimulation, heart mapping and visualization, delivery of pacemakers, and the like. These procedures generally rely on accurately navigating and placing instruments within a patient's vasculature.

During such procedures, a target vessel may be accessed using a guide wire advanced through the intervening vasculature into the target vessel, thereby providing a "railway" to the vessel. One or more instruments, e.g., catheters, sheaths, and the like, may be advanced over the guide wire or "rail" into a vessel, heart, artery, vein, and/or other body cavity or lumen.

In some cases, a sheath placed within a body cavity or lumen may then be used to deliver another device, such as a pacemaker lead, stent catheter, another sheath, and/or other device. Further, it may be desirable that such a delivery sheath exhibit certain properties, such as pushability, kink resistance, retention of shape, and/or durability in order to facilitate its own navigation into a body lumen or cavity and subsequent placement of a lead or device through it. Yet further, it may be desirable to maintain the stability of placement of a lead or device positioned within a body cavity or lumen while removing a delivery sheath. Removal is often accomplished by peeling, cutting, or slitting.

However, techniques (such as braid reinforcement) used to impart characteristics of pushability, kink resistance, and the like, may decrease the ease with which a sheath may be removed. For example, a braid reinforced sheath must generally be cut away using a slitter or other cutting tool, rather than peeled away as a non braid reinforced sheath might be. Further, cutting through a braid may be difficult or inconsistent, increasing the likelihood of dislodgment of a lead or other device during removal of the delivery sheath.

Accordingly, it may be useful to provide a delivery sheath that is pushable, kink resistant, and the like and/or that may be easily removed from a body while leaving a remaining lead or other device in place without substantially disturbing its placement.

BRIEF DESCRIPTION OF THE DRAWINGS

The drawings illustrate exemplary embodiments of the invention, in which.

DETAILED DESCRIPTION

Figures 1A, 1C:
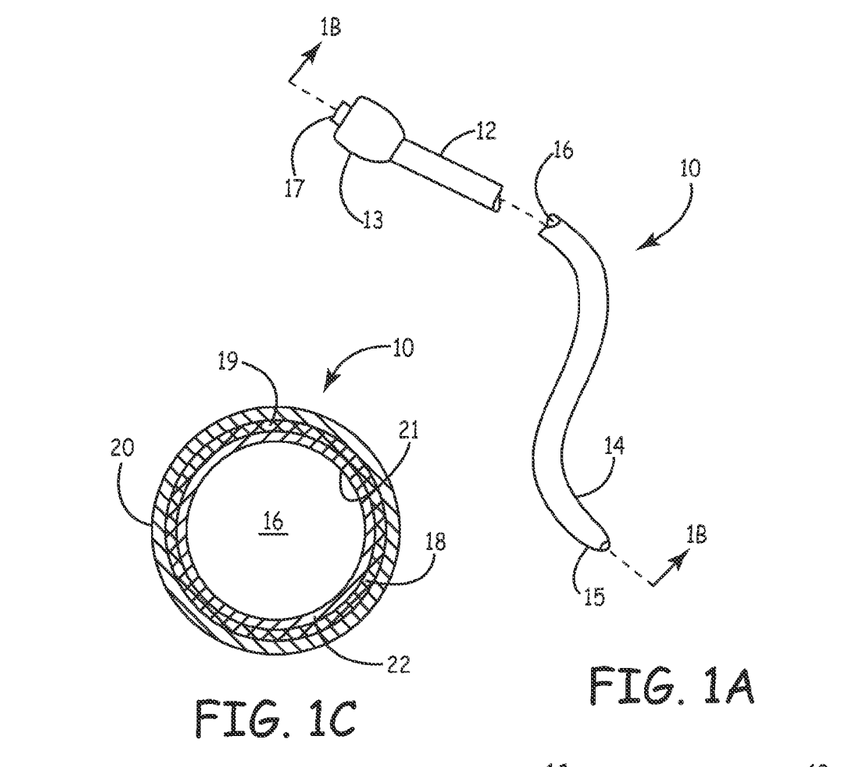
FIG. 1A is a perspective view of an exemplary embodiment of a tubular device, including a lumen extending between proximal and distal ends thereof.
FIG. 1C is a cross-sectional view of the tubular device of FIGS. 1A and 1B, taken along line 1C-1C of FIG. 1B.
Figure 1B:
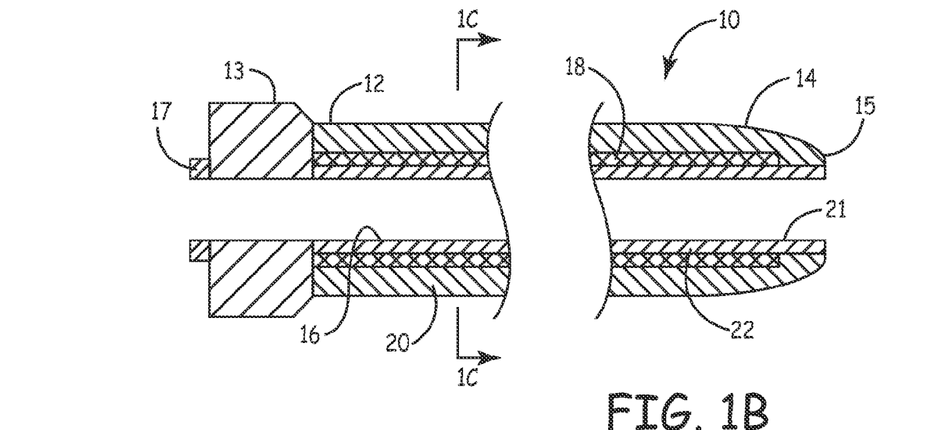
FIG. 1B is a cross-sectional view of the tubular device of FIG. 1A, taken along line 1B-1B, showing a reinforcing layer between an outer layer and a liner surrounding a lumen.

Turning to the drawings, FIGS. 1A-1C show an apparatus 10 for accessing a body lumen (not shown) and/or for delivering one or more fluids, agents, and/or instruments (also not shown) within a body lumen. In exemplary embodiments, the apparatus 10 may be a delivery sheath, a guide catheter, a procedure catheter, an imaging device, or other tubular device that may be peeled apart or otherwise separated during use. The apparatus 10 may be sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 is an elongate tubular member or device including a proximal end 12, a distal end 14 sized for insertion into a body lumen, and a lumen 16 extending between the proximal and distal ends 12, 14. Optionally, the apparatus 10 may include one or more additional lumens (not shown), which may be disposed concentrically around or side-by-side with the lumen 16. The lumen 16 may be sized for receiving a guide wire, procedure catheter, cardiac lead, needle, or other instrument (not shown), and/or for delivering fluids or other flowable agents or materials therethrough.

Optionally, the distal end 14 may include a tapered, rounded, or otherwise shaped distal tip 15, e.g., to provide a substantially atraumatic tip and/or facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Optionally, the proximal end 12 may include a handle 13 and/or one or more ports, e.g., port 17 communicating with the lumen 16. In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10.

Optionally, the apparatus 10 may include one or more backbones or support members (not shown) that may extend at least partially between the proximal and distal ends 12, 14, e.g., as disclosed in co-pending application Ser. Nos. 10/423,321, filed Apr. 24, 2003, and 11/347,361, filed Feb. 3, 2006, the entire disclosures of which are expressly incorporated by reference herein.

With particular reference to FIGS. 1B and 1C, the apparatus 10 generally includes a reinforcing layer 18 and an outer layer 20 surrounding the lumen 16. Generally, the reinforcing layer 18 includes one or more circumferential interruptions 19 (one shown in FIG. 1C) that may facilitate peeling or otherwise separating the apparatus 10, e.g., from around another device received within the lumen 16, as described further below.

Optionally, the apparatus 10 may include an inner layer 22, e.g., including a relatively thin film, sheet, or other material including an inner surface 21. The inner liner may be formed of a variety of materials to impart structural characteristics or for material properties. For example, a fluoro-polymer liner may be added to impart lubricity. Alternatively, a coated liner may be added for properties of lubricity, anti-thrombogenicity, hydrophilic characteristic, and the like, as disclosed in co-pending application Ser. No. 11/340,904, filed Jan. 26, 2006, the entire disclosure of which is expressly incorporated by reference herein. The layers of the apparatus 10 may be attached to one another, e.g., by laminating, adhering, adhesive bonding, ultrasonic welding, reflowing or other heating, and the like, as described elsewhere herein.

The construction of the apparatus 10 may be substantially uniform or may vary between the proximal and distal ends 12, 14 e.g., by varying the construction of the reinforcing layer 18, outer layer 20, and/or inner layer 22 along the length of the apparatus 10. In addition, the reinforcing layer 18 and/or the material of the outer layer 20 may allow the apparatus 10 to be twisted from the proximal end 12, e.g., to rotate the distal end 14 within a patient's body. Optionally, the outer layer 20, reinforcing layer 18, and/or inner layer 22 may include one or more sublayers (not shown), which may vary in construction in various portions of the apparatus 10.

In one exemplary embodiment, the proximal end 12 may be substantially rigid or semi-rigid, e.g., providing sufficient column strength to allow the apparatus 10 to be pushed from the proximal end 12, while the distal end 14 may be substantially flexible or semi-rigid. Thus, the distal end 14 of the apparatus 10 may be advanced or otherwise manipulated within a patient's body from the proximal end 12 without substantial risk of buckling and/or kinking. Optionally, the outer layer 20 at or adjacent the distal end 14 may be substantially flexible or semi-rigid and/or the reinforcing layer 18 may be terminated, e.g., to allow the distal end 14 to bend easily or otherwise be advanced through tortuous anatomy and/or provide a substantially atraumatic distal tip 15. For example, as shown in FIG. 1B, the reinforcing layer 22 may terminate within the distal end 14 proximal to the distal tip 15, e.g., to provide a relatively soft, flexible, and/or atraumatic distal tip 15.

In exemplary embodiments, the reinforcing layer 18 may include one or more round or flat wires, filaments, strands, braids, and the like. The material of the reinforcing layer 17 may be formed from metal, such as stainless steel, plastic, woven fibers, such as glass, Kevlar, and the like, or composite materials. Materials that may be used in the outer layer 20 may include one or more of PEBAX, urethane, FEP, PFA, polyethylene ("PE"), polyamide (Nylon), silicone, polypropylene, polysulfone, polyvinylchloride (PVC), polystyrene, polycarbonate, polymethylmethacrylate, fluoro-polymer, polyester, nylon, and the like. The inner layer 22 may include polyurethane, e.g., having a thickness between about 0.0001-0.01 inch (0.0025-0.25 mm), or other suitable polymers such as polyolefin, PEBAX, nylon, silicone, polypropylene, and polyethylene. Materials may be primarily selected for optimal mechanical, bonding, and/or other properties and subsequently imparted with desired surface properties, for example lubricity, by coating.

In exemplary embodiments, the apparatus 10 may have an outer diameter between about half and twenty millimeters (0.5-20 mm) or between about one and five millimeters (1-5 mm), and a length between about five and one hundred fifty centimeters (5-150 cm). The inner layer 22 may have a wall thickness between about 0.0001-0.01 inch (0.0025-0.25 mm) and the outer layer 20 may have a wall thickness between about 0.0005-0.2 inch (0.0127-5.08 mm).

FIGS. 2A-2E show a first embodiment of a tubular device 100 that generally includes an outer layer 105 and an interrupted tubular reinforcing structure 103 including a circumferential interruption 106. The tubular device 100 may be at least a portion of a delivery sheath or other apparatus, such as the apparatus 10 shown in FIG. 1A. In this embodiment, the circumferential interruption 106 is a longitudinal channel that extends substantially axially, e.g., at least partially between proximal and distal ends (not shown) of the tubular device 10.

Figure 2A:
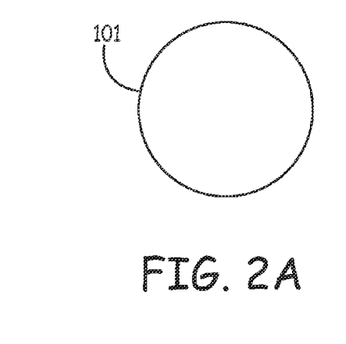
FIGS. 2A-2D are cross-sectional views showing a first method for making a circumferentially interrupted reinforcing layer.
Figures 2B, 2D:
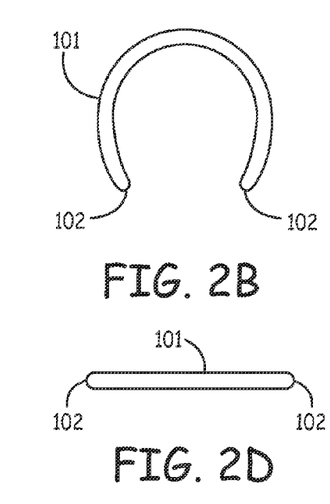
Figure 2C:
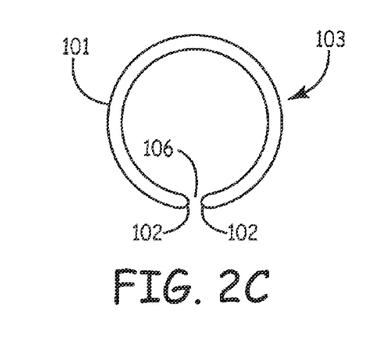

An exemplary method for making the reinforcing structure 103 is shown in FIGS. 2A-2C. Initially, as shown in FIG. 2A, an elongate tubular braid or other tubular reinforcing structure 101 may be provided. The tubular structure 101 may be a woven mesh, braid, or other material that may provide a desired reinforcement for the tubular device 100, e.g., formed from metal wire, such as stainless steel, Nitinol, and the like, having flat, round, or other geometric configurations, from polymer monofilaments, such as nylon and the like, and/or from other thread-like materials, such as twisted or woven synthetic or natural fibers.

Turning to FIG. 2B, the tubular braid 101 may be folded back onto itself to define two longitudinal edges 102. As shown in FIG. 2C, the tubular braid 101 may be folded or rolled, or the edges 102 may otherwise be brought together to define the longitudinal channel 106 between the edges 102. Alternatively, as shown in FIG. 2D, the tubular braid 101 of FIG. 2A may be flattened to define the longitudinal edges 106 after which the edges 102 may be brought together to form the interrupted tubular reinforcing structure 103 having the longitudinal channel 106. These methods for forming the interrupted tubular reinforcing structure 103 provide the advantage that they maintain the general integrity of the original tubular braid 101. Thus, the mechanical properties, e.g., the pushability, kink resistance, shape retention, and/or durability of the resulting tubular device 100 may be more easily defined and maintained. In addition, these methods avoid cutting fibers of the braid 101, which may otherwise unravel as a result of cutting, which may change the properties of the braid 101 and/or cause deterioration during manufacturing and/or use.

Figure 2E:
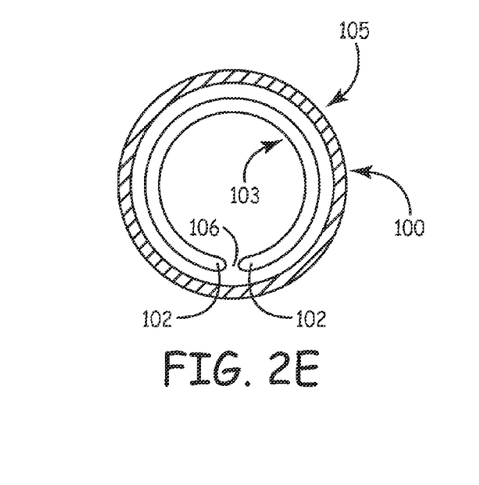
FIGS. 2E and 2F are cross-sectional views of tubular devices including the reinforcing layer of FIG. 2C.

Turning to FIG. 2E, the interrupted tubular reinforcing structure 103 may then be attached to a sheath body 105, e.g., to form composite tubular device 100, which may have enhanced properties compared to the sheath body 105 alone, e.g., enhanced pushability, kink resistance, retention of shape, and/or durability. The sheath body 105 may be formed similar to the outer layer 20 described above with reference to FIGS. 1A-1C. The interrupted tubular reinforcing structure 103 may be maintained within the sheath body 105 by friction fit, bonding with adhesive, reflowing to effectively incorporate the reinforcing structure 103 into the sheath body 105 to form a composite construction, and/or other methods such as those identified elsewhere herein. In an alternative embodiment, the interrupted tubular reinforcing structure 103 may be incorporated over the sheath body 105 (not shown) rather than within the sheath body 105 as shown.

The longitudinal channel 106 may have a relatively small width compared to the circumference of the tubular device 100. Once the reinforcing structure 103 is attached to the sheath body 105, the longitudinal channel 106 may be filled with material, e.g., adhesive, material from the sheath body 105 that may flow into the longitudinal channel 106, and the like. Alternatively, the ends 102 of the braid 101 may even abut one another yet provide a circumferential interruption 106, i.e., a circumferential discontinuity in the reinforcing structure 103 that extends longitudinally along the tubular device 100.

The longitudinal channel or circumferential interruption 106 of the interrupted tubular reinforcing structure 103 may facilitate removing the tubular device 100, e.g., from around another device received within the tubular device 100, such as a pacing lead (not shown). For example, the tubular device 100 (or apparatus 10 of FIGS. 1A-1C incorporating the tubular device 100) may be introduced into a body lumen (not shown). In one embodiment, the apparatus 10 may be introduced into a patient's body via a percutaneous puncture and advanced through the patient's vasculature into the heart, e.g., through the right atrium, coronary, sinus, and into the coronary veins to access a target delivery site. Another device, e.g., a pacing lead (not shown), may be introduced through the lumen 16 of the apparatus 10 until the device is delivered to the target delivery site. Once the device, e.g., lead, is properly positioned, the apparatus 10, including the tubular device 100, may be split along the circumferential interruption 106 to facilitate removing the apparatus 10 from around the delivered device.

For example, a slitter or other cutting device (not shown) may cut along the circumferential interruption 106, i.e., passing between the ends 102 of the braid 101, thereby only cutting through the sheath body 105 and not the combined sheath body 105 and reinforcing structure 103. With particular reference to FIG. 1A, the slitter may be positioned at the proximal end 12 of the tubular device 10 and aligned with the circumferential interruption 106 in FIG. 2E. The slitter may then be advanced distally and/or the tubular device 10 may be pulled proximally to cause the slitter to cut through the sheath body 105 along the circumferential interruption 106, i.e., along the longitudinal channel 106 and/or between the ends 102 of the reinforcing structure 103.

In an exemplary embodiment, a slitter may be incorporated into the handle 13 and/or otherwise into the proximal end 12 of the apparatus 10 such that the slitter is furnished to the user aligned with the circumferential interruption 106. Otherwise, a guide element, e.g., a groove, slot, pocket, and the like, and/or a visual indicator (not shown) may be provided on the proximal end 12 of the apparatus 10 that may facilitate the user aligning a slitter with the circumferential interruption 106. Thus, when the slitter is aligned with the guide element, the slitter is aligned with the circumferential interruption 106. Exemplary handles and/or slitters that may be provided are disclosed in co-pending application Ser. No. 10/958,034, filed Oct. 4, 2004, the entire disclosure of which is expressly incorporated by reference herein.

Figure 2F:
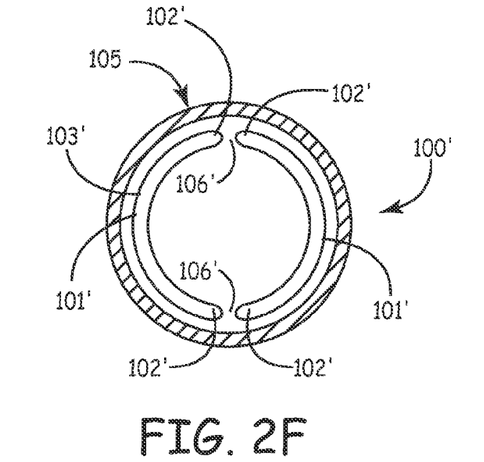
Figure 4:
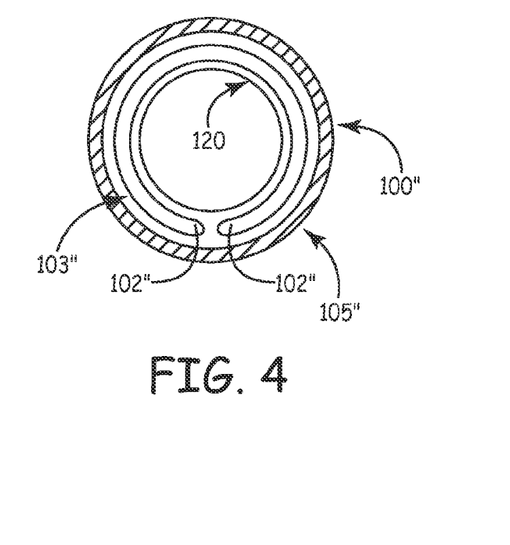
FIG. 4 is a cross-sectional view of a tubular device including a circumferentially interrupted reinforcing layer including two reinforcing structures similar to those shown in FIGS. 2A-2D.

Turning to FIG. 2F, an alternative embodiment of a tubular device 100' is shown that is constructed similar to the tubular device 100 shown in FIGS. 2A-2E. Unlike the previous embodiment, the tubular device 100' includes a circumferentially interrupted reinforcing layer 103' that includes two circumferential interruptions 106.' Initially, two tubular braids 101' may be provided that may be folded and rolled to define longitudinal edges 102.' The two folded and rolled braids 101' are then placed within a sheath body 105 such that the longitudinal edges 102' of the braids 101' are disposed adjacent one another, thereby defining two longitudinal channels 106.' As shown, the tubular braids 101' may have similar diameters such that they each define approximately half of the interrupted reinforcing layer 103.' Alternatively, the tubular braids 101' may have different diameters, e.g., if it is desired to place the circumferential interruptions 106' other than opposite one another. It will be appreciated that more than two circumferential interruptions 106' may be provided, if desired. In a further alternative, shown in FIG. 4, an inner layer 120 is shown within a tubular device 100" that includes a circumferentially interrupted reinforcing layer 103" including a single circumferential interruption 106."

Figure 3A:
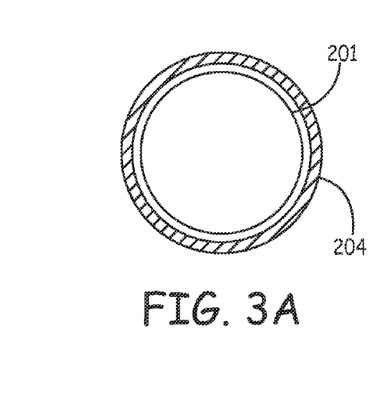
FIGS. 3A and 3B are cross sectional views showing another method for making a circumferentially interrupted reinforcing layer.
Figure 3B:
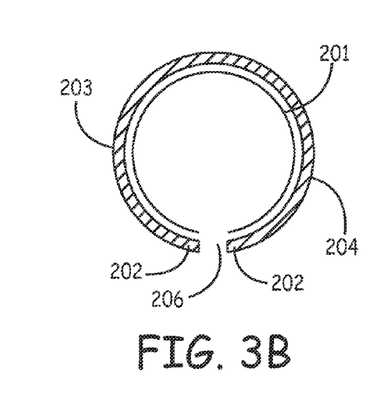
Figure 3C:
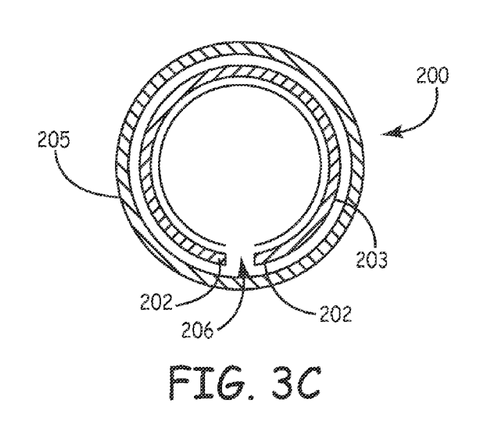
FIG. 3C is a cross-sectional view of a tubular device including the reinforcing layer of FIG. 3C.

Turning to FIGS. 3A-3C, another embodiment of a tubular device 200 is shown that generally includes a circumferentially interrupted reinforcing layer 203 and a sheath body 205, similar to the previous embodiments. Unlike the previous embodiments, the reinforcing layer 203 includes a composite structure. As shown in FIG. 3A, a tubular braid 201, which may be similar to those described above (or other reinforcing material), may be attached to a tubular structure 204, which may be constructed similar to the outer layer described above. As shown, the tubular braid 201 is placed inside the tubular structure 204 and the two layers are incorporated to form a composite construction, e.g., using methods described elsewhere herein. Alternatively, the tubular braid 201 may attached or placed around the tubular structure 204, rather than within in.

Turning to FIG. 3B, the composite construction is then cut to create a longitudinal channel 206 defined by opposing longitudinal edges 202, thereby creating the circumferentially interrupted reinforcing layer 203. Once cut, the longitudinal edges 202 may abut one another, yet be free to separate from one another. Alternatively, some of the composite construction may be removed along the longitudinal channel 206 such that the longitudinal edges 202 remain spaced apart from one another by a desired distance. Turning to FIG. 3C, the reinforcing layer 203 may then be placed within a sheath body 205, which may be similar to the outer layer described above. The reinforcing structure 203 and sheath body 205 may be attached, e.g. using an adhesive, heat, and/or other methods for bonding or reflowing the materials.

Optionally, during this step, the width of the longitudinal channel 106 may be controlled, e.g., using an elongate spacer (not shown). For example, an elongate rod or tube (not shown) may be inserted through the interior of the reinforcing layer 203 that has a diameter slightly larger than the lumen, thereby causing the longitudinal edges 202 to separate a desired distance. The bonding, reflowing, or other process used to attach the sheath body 205 and the interrupted tubular reinforcing structure 203 may then be completed, whereupon the spacer may be removed.

Figure 3D:
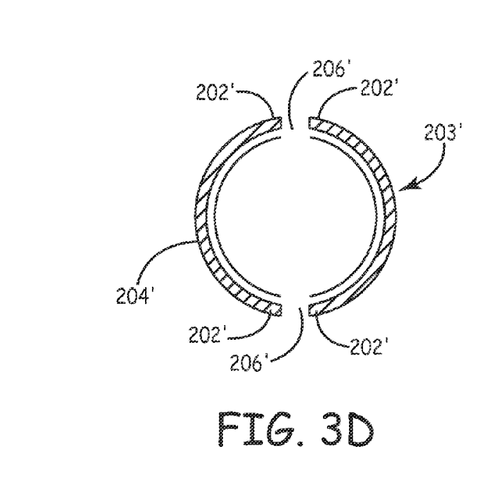
FIG. 3D is a cross-sectional view of a circumferentially interrupted reinforcing layer including two circumferential interruptions.
Figure 3E:
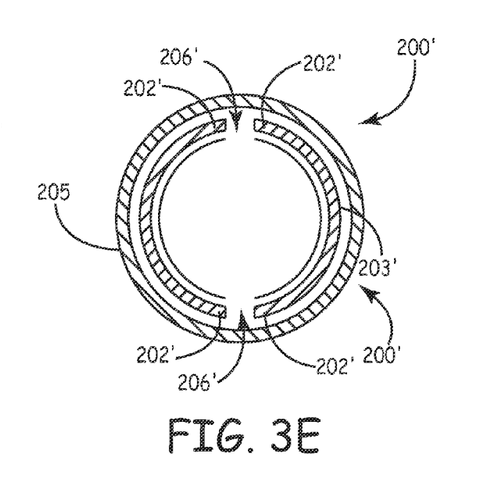
FIG. 3E is a cross-sectional view of a tubular device including the reinforcing layer of FIG. 3D.

Turning to FIGS. 3D and 3E, a sheath or tubular device 200' may be provided that includes multiple reinforcing structures and/or multiple longitudinal channels or circumferential interruptions 206.' For example, a composite construction including a tubular braid 201' and a tubular structure 204' may be formed, similar to the embodiment shown in FIG. 3A. The composite construction may then be cut longitudinally at multiple locations, e.g., at two circumferentially opposite locations, as shown in FIG. 3D, to provide two longitudinal channels 206.' Thus, the circumferentially interrupted reinforcing layer 203' may include two reinforcing structures, each approximately semi-circular in cross-section, leaving two longitudinal channels 206.' The two structures may then be attached to a sheath body 205' similar to the previous embodiments, as shown in FIG. 3E.

In this manner, a tubular device 200' may be provided that may be removed from around another device by peeling or separating the tubular device 200' into two pieces, rather than slitting or cutting. For example, with additional reference to FIG. 1A, the handle 13 may include two handles, tabs, elongated ends, or other components attached to the proximal end 12 opposite one another over the two reinforcing structures, which may facilitate a user gripping when pulling apart or peeling away the tubular device 200.' If the two components are pulled away from one another (transversely relative to the longitudinal axis 18), the tubular device 200' may separate at the longitudinal channels 206 initially at the proximal end 12 and propagating towards the distal end 14 of the apparatus 10, thereby separating the tubular device 200. Peeling apart may be facilitated by longitudinally scoring the tubular structure 204' and/or the sheath body 205,' e.g., along the area overlying the longitudinal channels 206.'

Figure 5:
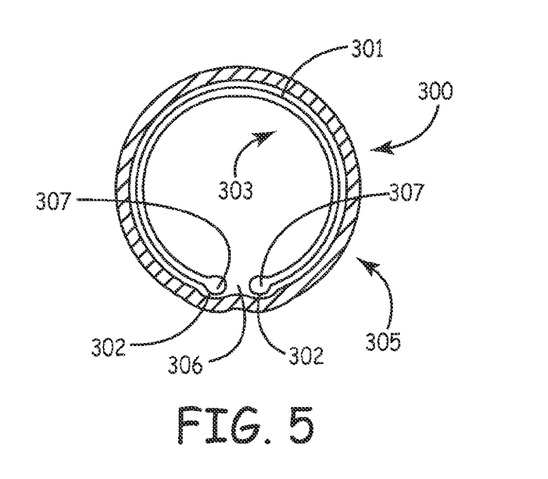
FIG. 5 is a cross-sectional view of a tubular device including a circumferentially interrupted reinforcing layer that defines lumens.

Turning to FIG. 5, another embodiment of a reinforced tubular device 300 is shown that is generally constructed similar to the embodiments shown in FIGS. 2A-2E. For example, the tubular device 300 generally includes a circumferentially interrupted reinforcing layer 303 and a sheath body 305 attached to one another. The reinforcing layer 303 may be formed from a tubular braid 301 that is folded and rolled into itself to define longitudinal edges 302 that define a circumferential interruption 306. Unlike the previous embodiments, the tubular device 300 includes one or more lumens 307, e.g., formed at one or both of the longitudinal edges 302 of the tubular braid 301.

For example, when (during or after) the tubular braid 301 is folded and rolled, an elongate mandrel, e.g., a wire, tube, rod, and the like (not shown) may be placed within one or both of the loops defining the longitudinal edges 302 of the tubular braid 301. With the mandrel(s) within the longitudinal edges 302, the reinforcing layer 303 may be formed and/or the reinforcing layer 303 may be attached to the sheath body 305. Once the reinforcing layer 303 is attached to the sheath body 305 to provide the tubular device 300, the mandrel(s) may be removed, thereby providing one or two lumens extending along the tubular device 300 adjacent the main lumen. If multiple tubular braids are used to provide the reinforcing layer 303, it may be possible to provide more than two lumens, if desired. These lumens, formed in the wall of the tubular device 300, may be used for infusion of fluids, placement of electrical conducting wires, carrying pull wires, for example, in order to construct a steerable sheath, and the like.

Figure 6A:
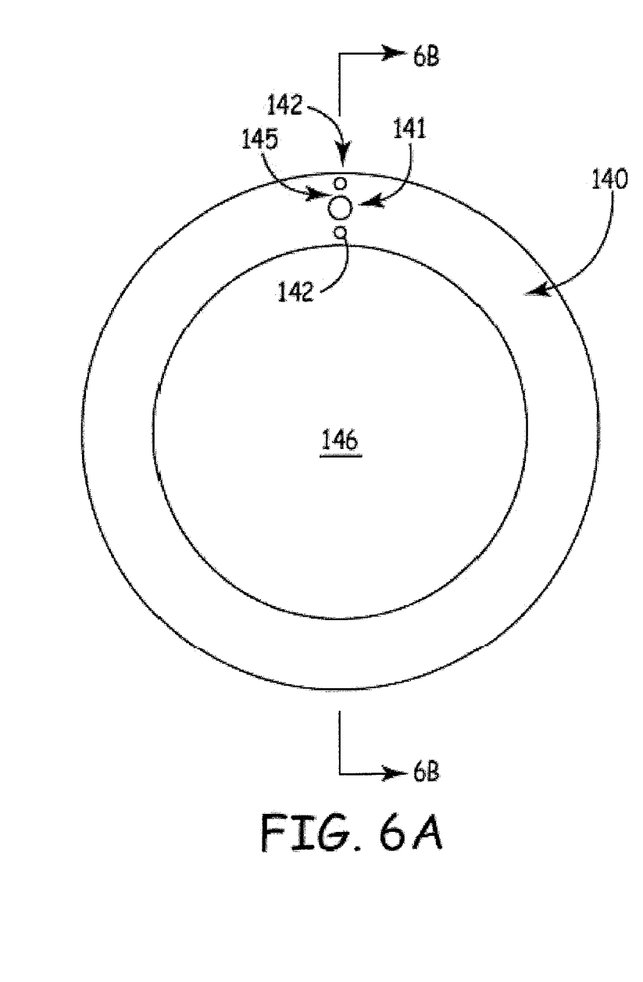
FIG. 6A is a cross-sectional view of another embodiment of a tubular device including ripcord channels.
Figure 6B:
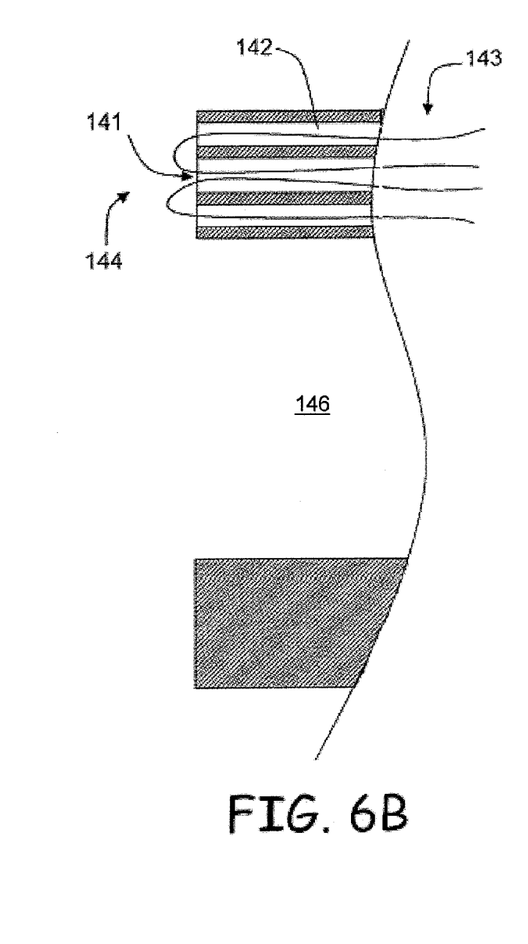
FIG. 6B is a cross-sectional view, through section line 6B-6B of FIG. 6A, of a distal portion of the tubular device including ripcords.

Turning to FIGS. 6A and 6B, yet another embodiment of a tubular device 140 is shown that may be incorporated into an apparatus, such as apparatus 10 of FIGS. 1A-1C. Generally, the tubular device 140 may be a sheath body that includes one or more ripcord channels 141, 142 in its outer wall 145. One or more ripcords 143 may be placed within the ripcord channels 141, 142, running longitudinally through the tubular device 140. As shown, the ripcords 143 may run through respective peripheral lumens 142 from a proximal end (not shown) of the tubular device 140 (e.g., from proximal end 12 of apparatus 10 shown in FIG. 1A) to a distal end 144 of the tubular device 140, and then wrap around and return to the proximal end of the tubular device 140 through central channel 141 (e.g., back to the proximal end 12).

After using the apparatus 10 to deliver a lead or other device (not shown) through a main lumen 146, which corresponds to lumen 16 of apparatus 10, the ripcords 143 may be pulled (e.g., from the proximal end 12 of the apparatus 10), causing the ripcords 143 to tear through the wall 145 between the two channels 141, 142 and creating a longitudinal weakness or interruption in the tubular device 140 along which the tubular device 140 may be peeled or torn away, e.g., from a lead or other device (not shown) extending through the main lumen 146, as described previously. The ripcords 143 may be formed from metal wire, such as stainless steel, Nitinol, and the like, having flat, round or other geometric configurations, from polymer monofilaments, such as nylon and the like, or from other thread-like materials, such as twisted or woven synthetic or natural fibers. The sheath body 140 may be constructed of the same materials enumerated with regard to the outer layer and the other embodiments described above. Alternatively, the ripcords 143 may themselves effectively comprise the wall of the tubular device 140 on either side of the central channel 141 such that pulling the ripcords effectively separates the tubular device 140 longitudinally allowing the tubular device 140 to be removed from around a lead or device without requiring any further pealing or tearing of the tubular device 140. The ripcords 143 may be embedded within the wall of the tubular device 140, e.g., when the tubular device 140 is molded, extruded, or otherwise formed. Optionally, if additional longitudinal tears or weaknesses are desired, multiple ripcords (not shown) may be provided along the length of the tubular device 140, e.g., at other locations around the circumference of the tubular device 140. Alternatively, if desired, only a single ripcord 143 may be provided (not shown).

Figure 7A:
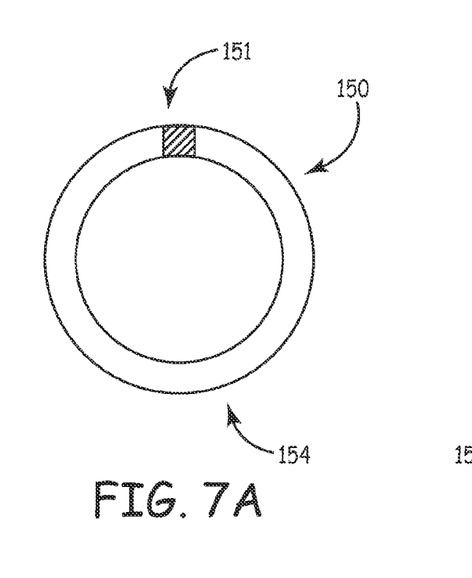
FIGS. 7A and 7B are cross-sectional views of alternative embodiments of tubular devices that include different materials co-extruded together to facilitate peeling the tubular devices apart.
Figure 7B:
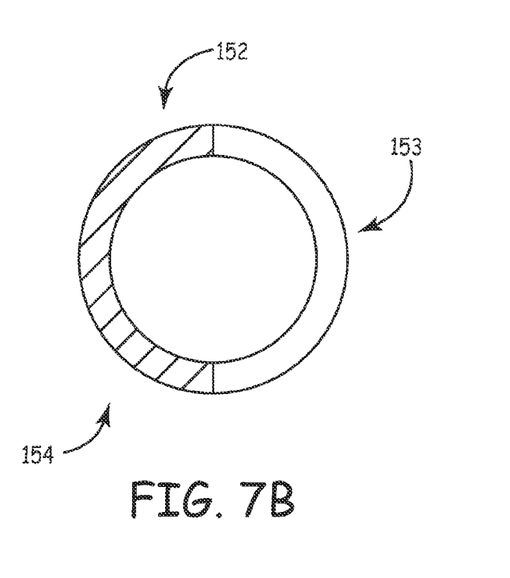

Turning to FIGS. 7A and 7B, yet another embodiment of a peelable or tearable sheath body or tubular device 154 is shown. The sheath body 154 may be co-extruded using two different materials 150, 151 (as shown in FIG. 7A) or 152, 153 (as shown in FIG. 7B). The materials may exhibit decreased bonding strength or a differential in structural properties such that a natural parting line is formed between them, thus enabling the sheath body 154 to be more easily peeled or torn longitudinally. Alternatively, a single material may be utilized but modified with various additives to provided a similar decrease in bonding and/or differential in structural properties. For example, one part 151, 152 of the sheath body 154 may be constructed of an un-modified PEBAX. The other part 150, 153 of the sheath body 154 may be constructed of a modified PEBAX having additives to decrease its ability to bond to the unmodified PEBAX. For example, a fluoro-polymer oil may be added.

Alternatively or in addition, modification of structural properties may be accomplished by adding clay or glass in order to increases tensile strength and decrease elongation of the modified material (for example, urethane or PEBAX) such that, when extruded next to an un-modified material (for example urethane or PEBAX), the differential properties may cause a natural part line during peeling away, thus facilitating easier removal of the sheath body 154 from around a lead or other device (not shown) delivered into a body lumen (also not shown) using the sheath body 154, as described elsewhere herein. In addition to the particular configurations shown in FIGS. 7A and 7B, it is envisioned that other embodiments may include different configurations of two or more materials having differential properties to accomplish the same end result.

Figures 8A, 8B:
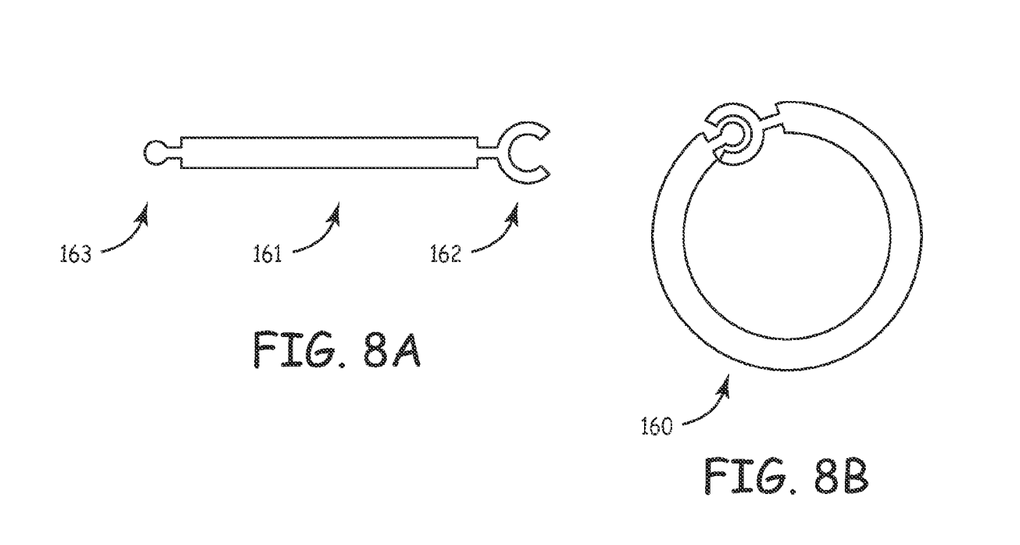
FIGS. 8A and 8B are cross-sectional views showing a method for making another embodiment of a tubular device formed from a sheet including ends that interlock when the sheet is rolled into a tubular shape.

Referring to FIGS. 8A and 8B, yet another embodiment of a peelable or tearable sheath body or tubular device 160 is shown. Generally, the sheath body 160 is constructed from an elongate panel, sheet, or other member having an initially flat cross-section 161 with interlocking features 162, 163 extending along opposite longitudinal edges. The sheath body 160 may be formed by wrapping the flat member around a mandrel or other structure or rolling the flat member until the longitudinal edges 162, 163 are disposed adjacent one another, e.g., to form a substantially circular cross-section. The interlocking features on the longitudinal edges 162, 163 may be engaged with one another to maintain the sheath body 160 in its tubular shape. The mandrel, if used, may be removed, and the sheath body 160 incorporated into an apparatus, such as the apparatus 10 of FIGS. 1A-1C.

After using the sheath body 160 (or apparatus incorporating the sheath body 160) to deliver a lead or other device, the sheath body 160 may then be easily removed by applying enough force to pull apart the two interlocking longitudinal edges 162, 163 while leaving behind the lead or other device positioned within the body. This separation may be facilitated by providing tabs, elongated ends, handles, or other similar features (not shown) on the proximal end of the sheath body 160 (e.g., on the handle 13 shown in FIG. 1A) to facilitate initiation and propagation of the peeling action (e.g., towards the distal end 14). The sheath body 160 may be constructed using similar materials and methods to those described elsewhere herein.

Figure 9A:
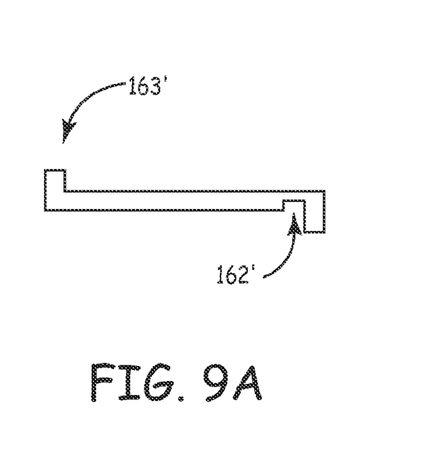
FIGS. 9A and 9B are cross-sectional views showing another method for making another embodiment of a tubular device formed from a sheet including ends that interlock when the sheet is rolled into a tubular shape.
Figure 9B:
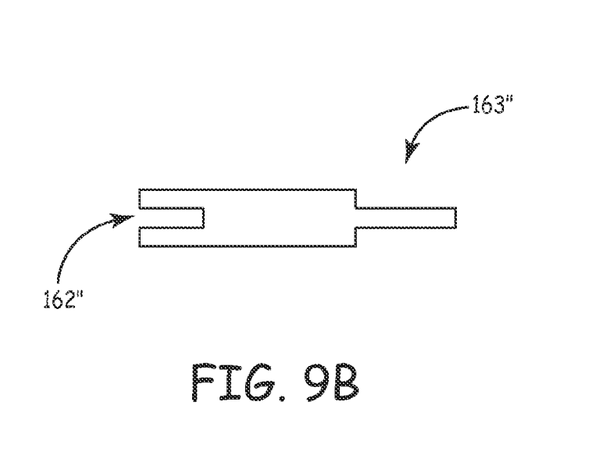

FIGS. 8A and 8B show interlocking edges that includes a generally "C" shaped pocket and a cylindrical tab that may be received within the pocket. Alternatively, FIG. 9A shows another embodiment in which longitudinal edge 163' includes a flange, and longitudinal edge 162' includes a pocket for receiving the flange. In a further alternative, FIG. 9B shows another embodiment in which longitudinal edge 163" includes a tongue, and longitudinal edge 162" includes a groove for receiving the tongue. Thus, the longitudinal edges may be removably engaged with one another. The longitudinal edges may be held together simply by friction and/or an interference fit. Alternatively, a weak adhesive or other material may be It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A sheath for delivering a lead or other device into a body lumen of a patient, comprising:
    an elongate tubular member including a proximal end, a distal end sized for introduction into a body lumen, and an outer wall defining a main lumen that extends longitudinally between the proximal and distal ends, the wall including a first channel and a second channel, the first and second channels extending within the wall, directly alongside one another, and longitudinally between the proximal and distal ends; and
    a ripcord that extends through the first channel, from the proximal end to the distal end of the tubular member, and wraps around, at the distal end, to extend through the second channel from the distal end to the proximal end, such that, when the ripcord is pulled from the proximal end, the ripcord tears through the wall, between the first and second channels.

2. The sheath of claim 1, further comprising:
    another ripcord; and
    wherein the outer wall further includes a third channel that extends within the wall and directly alongside the second channel, longitudinally between the proximal and distal ends; and
    the other ripcord extends through the third channel from the proximal end to the distal end, and wraps around, at the distal end, to extend through the second channel from the distal end to the proximal end, such that when the other ripcord is pulled from the proximal end, the other ripcord tears through the wall, between the third and second channels.

3. The sheath of claim 2, wherein the second channel is positioned in between the first and third channels.

* * * * *